United States Patent
Stowell et al.

(10) Patent No.: US 9,441,001 B2
(45) Date of Patent: Sep. 13, 2016

(54) METHOD OF MAKING HYDROXYMETHYLPHOSPHONATE, POLYURETHANE FOAM-FORMING COMPOSITIONS, POLYURETHANE FOAM AND ARTICLES MADE THEREFROM

(71) Applicant: ICL-IP AMERICA INC., Ardsley, NY (US)

(72) Inventors: Jeffrey K. Stowell, Wingdale, NY (US); Gerardo Francisco, Orangeburg, NY (US); Edward Weil, Copley, OH (US)

(73) Assignee: ICL-IP America Inc., Tarrytown, NY (US)

( * ) Notice: Subject to any disclaimer, the term of this patent is extended or adjusted under 35 U.S.C. 154(b) by 64 days.

(21) Appl. No.: 14/368,646

(22) PCT Filed: Sep. 12, 2013

(86) PCT No.: PCT/US2013/059358
§ 371 (c)(1),
(2) Date: Jun. 25, 2014

(87) PCT Pub. No.: WO2014/062313
PCT Pub. Date: Apr. 24, 2014

(65) Prior Publication Data
US 2014/0378564 A1    Dec. 25, 2014

Related U.S. Application Data

(60) Provisional application No. 61/715,030, filed on Oct. 17, 2012.

(51) Int. Cl.
| | | |
|---|---|---|
| *C07F 9/40* | (2006.01) | |
| *C08L 75/04* | (2006.01) | |
| *C08J 9/00* | (2006.01) | |
| *C08K 5/5333* | (2006.01) | |
| *C08G 18/08* | (2006.01) | |

(52) U.S. Cl.
CPC .......... *C07F 9/4003* (2013.01); *C07F 9/4006* (2013.01); *C08G 18/14* (2013.01); *C08J 9/0038* (2013.01); *C08K 5/5333* (2013.01); *C08L 75/04* (2013.01); *C08J 2375/04* (2013.01)

(58) Field of Classification Search
CPC .... C07F 9/4003; C07F 9/4006; C08G 18/14; C08K 5/5333; C08L 75/04; C08J 9/0038; C08J 2375/04
See application file for complete search history.

(56) References Cited

U.S. PATENT DOCUMENTS

| | | |
|---|---|---|
| 2,579,810 A | 12/1951 | Fields |
| 2,593,213 A | 4/1952 | Stiles |
| 3,102,900 A | 9/1963 | Fields |
| 3,179,522 A | 4/1965 | Temin |
| 3,382,301 A | 5/1968 | Hechenbleikneret et al. |
| 3,385,801 A | 5/1968 | Birum et al. |
| 3,609,107 A | 9/1971 | Boyer et al. |
| 4,024,207 A | 5/1977 | Biehler et al. |
| 4,697,030 A | 9/1987 | Hardy et al. |
| 4,808,744 A * | 2/1989 | Hardy .................. C07F 9/4006 558/163 |
| 4,820,854 A | 4/1989 | Hardy et al. |
| 4,883,891 A | 11/1989 | Hardy et al. |
| 4,883,892 A | 11/1989 | Hardy et al. |
| 4,886,895 A | 12/1989 | Hardy et al. |
| 5,097,057 A | 3/1992 | Hardy et al. |
| 5,117,033 A | 5/1992 | Hardy et al. |
| 5,272,128 A | 12/1993 | Rosen et al. |
| 5,952,327 A | 9/1999 | Waldeck et al. |
| 6,380,273 B1 * | 4/2002 | Eilbracht ............... C08J 9/0038 521/106 |
| 8,198,341 B2 | 6/2012 | Stowell et al. |
| 2007/0112084 A1 | 5/2007 | Hansel et al. |
| 2009/0203942 A1 * | 8/2009 | Hadjikyriacou .......... C07F 9/08 568/14 |
| 2010/0160468 A1 | 6/2010 | Stowell et al. |

FOREIGN PATENT DOCUMENTS

| | | |
|---|---|---|
| CA | 2246634 | 4/1999 |
| EP | 0570706 | 11/1993 |
| EP | 0908464 EP | 4/1999 |
| GB | 682706 | 11/1952 |
| GB | 1420543 | 1/1976 |
| WO | 2014/056138 A1 | 4/2014 |
| WO | 2014/062313 A1 | 4/2014 |

OTHER PUBLICATIONS

Ivanov et al, "Reaction in the System Trialkyl Phosphite—Carboxamide or Secondary Amine," Bulletin of the Academy of Sciences of the USSR, Division of Chemical Science, vol. 20, No. 12, Dec. 1971, pp. 2629-2632.

Gajewiak et al, "Synthesis and Molecular Recognition of the Phosphatidylinositol-3-Methylenephosphate," Organic Letters, vol. 8, No. 13, Jun. 22, 2006, pp. 2611-2813.

International Search Report dated Nov. 25, 2013.

* cited by examiner

*Primary Examiner* — John Cooney
(74) *Attorney, Agent, or Firm* — Dilworth & Barrese, LLP

(57) ABSTRACT

There is provided herein a method of making hydroxymethylphosphonate comprising reacting paraformaldehyde, at least one dialkyl phosphite and at least one trialkyl phosphite, in the presence of at least one amine catalyst.

14 Claims, No Drawings

US 9,441,001 B2

METHOD OF MAKING HYDROXYMETHYLPHOSPHONATE, POLYURETHANE FOAM-FORMING COMPOSITIONS, POLYURETHANE FOAM AND ARTICLES MADE THEREFROM

This application is a U.S. National Phase application of PCT Application No. PCT/US13/59358 filed on Dec. 12, 2013 which claims priority to U.S. Provisional Application No. 61/715,030 filed on Oct. 17, 2012.

BACKGROUND OF THE INVENTION

1. Field of the Invention

The present invention relates to a method of making hydroxymethylphosphonates, polyurethane foam-forming compositions containing the same, polyurethane foam formed from the polyurethane foam-forming compositions, and polyurethane foam articles made therefrom.

2. Description of Related Art

Polyurethanes are materials that are suitable for a large number of different applications in the industrial and private sectors. However, their use presents problems whenever it is involved in areas where there is a risk of fire. To modify their fire behavior, flame-retarding agents are usually added to these polyurethane materials.

Phosphorus compounds are highly effective flame-retarding agents for polyurethane foam, owing to their high phosphorous content and good compatibility with polyurethane systems. Unfortunately, various phosphorus-based flame retardants have various processing problems associated with their use. Hydroxymethylphosphonates have found some use as flame-retarding agents but their use has been severely limited by their problematic synthesis, low purity, and specifically their content of acidic by-products and water. Further, the formation of hydroxymethylphosphonates has previously been conducted very quickly, and in small batches, due to extreme exotherms, which occur in the production of such hydroxymethylphosphonates, which exotherms can result in high acid content. Other attempts to produce hydroxymethylphosphonates have necessitated extremely high reaction temperatures. Still other attempts to produce hydroxymethylphosphonates have resulted in significant byproducts and/or low product yields. Therefore, there is a need for a means of making hydroxymethylphosphonates, which avoids these quality and processing difficulties.

BRIEF SUMMARY OF THE INVENTION

There is provided herein a method for making hydroxyalkylphosphonate(s), specifically, hydroxymethylphosphonate(s), which method results in a high purity, low water and low acidity product that as a result has improved processing and storage stability characteristics. The hydroxymethylphosphonate made by the method herein has a reduced acidity and significantly reduced water content rendering it significantly advantageous to polyurethane foam applications. In addition, the method herein, in one embodiment, can be conducted with a less costly unhindered amine catalyst.

Specifically, there is provided herein a method of making hydroxymethylphosphonate comprising reacting paraformaldehyde, at least one dialkyl phosphite and at least one trialkyl phosphite, in the presence of at least one amine catalyst.

More specifically, the method further comprises heating paraformaldehyde in a solvent to a desired reaction temperature, wherein the solvent is present in at least an amount necessary to solvate or suspend the paraformaldehyde; adding at least one dialkyl phosphite and at least one trialkyl phosphite to the heated paraformaldehyde, to provide hydroxymethylphosphonate, there being present in the reaction medium at least one amine catalyst e.g., in a preferred example an amine whose nitrogen atom is directly bound to a secondary and/or tertiary carbon of an organic group, e.g., an alkyl group of from 1 to about 8 carbon atoms; and, optionally, following the completion of the addition, heating the reaction mixture to an elevated temperature.

In one embodiment, the method herein can be conducted in the absence of a solvent, such as the non-limiting embodiment wherein one or more of the amine, the dialkyl phosphite and the trialkyl phosphite component(s) function as a medium, e.g., for the solid paraformaldehyde, so that the reaction can occur in the liquid state.

It will be understood herein that organic moieties can comprise any linear, branched, or cyclic alkyl groups, alkenyl groups, alkynyl groups, aromatic groups, and any of the aforesaid containing a heteroatom, such as, for example, oxygen, nitrogen, or sulfur, wherein said groups can contain up to about 18 carbon atoms, specifically up to about 12 carbon atoms and most specifically up to about 10 carbon atoms.

DETAILED DESCRIPTION OF THE INVENTION

The inventors herein have unexpectedly discovered that the reaction of dialkyl phosphite and trialkyl phosphite, with paraformaldehyde (suspended or solvated and heated, or in another embodiment, not suspended and/or solvated in a solvent (i.e., in the instance wherein the method is conducted in the absence of solvent) and then heated), in the presence of an amine catalyst, can in fact produce hydroxymethylphosphonate with a lower level of water and acid content than an equivalent method which is conducted in the absence of trialkyl phosphite, especially when conducted at a temperature of 75 degrees Celsius or above. The presence of water during the reaction and after the reaction (e.g., during product storage) promotes hydrolysis of the dialkyl hydroxymethylphosphonate product forming a higher acidity product. By including trialkyl phosphite, the hydroxymethylphosphonate product contains less water present in the product, and thus, the shelf-life stability of the product is greatly improved.

In one embodiment, the use of the generally more costly hindered amine catalyst dramatically reduces the quaternization of such catalyst by the alkyl phosphite components (dialkyl phosphite and trialkyl phosphite), resulting in extended catalyst life and more controlled reaction conditions, yielding a higher purity product. The use of unhindered amines in reactions of dialkyl phosphite and paraformaldehyde has previously required that the reaction be run at high speed to avoid the quaternization of the catalyst. To achieve this high speed of reaction to avoid catalyst quaternization, typically the reaction components were combined at once and reacted very quickly resulting in high reaction temperatures, which high temperature reaction results in undesirable by-products and/or acidic by-products.

Such a method of the immediate complete addition of one of the reaction components to the other in the presence of unhindered amine catalyst and previously unappreciated absence of a trialkyl phosphite results in a dramatic reaction exotherm, dramatically limiting the batch size, and causing the resulting product from such a immediate addition to hydrolyze at high temperatures in the presence of water liberated from the paraformaldehyde, leading to an unacceptably high level of acidic by-product, e.g., greater than 20 mg KOH/g.

In one embodiment herein, the use of hindered amine catalyst in the reaction mixture in which addition of dialkyl phosphite and trialkyl phosphite to heated suspended paraformaldehyde occurs, allows for a lower reaction temperature, and slower addition, that avoids an excessive exotherm, the production of acidic by-products and previously unexpected reduced production of water during the reaction process.

In another embodiment, the use of trialkyl phosphite to replace a portion, e.g., 10 weight percent of the dialkyl phosphite alternatively permits the method to be run with a less costly unhindered amine catalyst (or optionally, still with a hindered amine catalyst) and at a fast reaction rate and high temperature, e.g., in excess of 75 degrees Celsius, to provide product hydroxymethylphosphonate without undesirable acidic byproducts and water.

It will be understood herein that all ranges herein include all subranges there between and also any combination of endpoints of said ranges.

It will be understood herein that the expression linear or branched divalent alkylene group comprises a saturated linear or branched alkyl group which has sufficient hydrogen atoms removed therefrom to allow the alkyl group to be divalent.

It will be understood herein that the expression linear or branched divalent alkenylene group comprises an alkenyl group which has sufficient hydrogen atoms removed therefrom to allow the alkyl group to be divalent.

Unless indicated otherwise, all weight percentages herein are based on the total weight of the reaction components.

All temperatures herein are room temperature unless indicated otherwise.

The hydroxymethylphosphonate can be any hydroxymethylphosphonate, which is made by the method(s) described herein.

Preferably, the hydroxymethylphosphonate is one or more of the general formula:

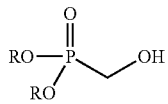

and/or, the general formula:

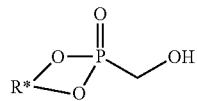

wherein each R is independently the same or different, linear or branched alkyl group of from 1 to about 8 carbon atoms, preferably from 1 to about 6 carbon atoms, and more preferably from 1 to about 3 carbon atoms, linear or branched alkenyl group of from 2 to about 10 carbon atoms, and more preferably from about 3 to about 8 carbon atoms, cycloalkenyl group of from about 5 to about 10 carbon atoms, and more preferably from about 5 to about 8 carbon atoms, and, cycloalkyl group of from about 5 to about 10 carbon atoms, and, more preferably from about 5 to about 8 carbon atoms; and R* is a linear or branched divalent alkylene group of from 2 to about 10 carbon atoms, preferably from 3 to about 8 carbon atoms, linear or branched divalent alkenylene group of from 2 to about 10 carbon atoms, and more preferably from about 3 to about 8 carbon atoms, divalent cycloalkenyl group of from about 5 to about 10 carbon atoms, and more preferably from about 5 to about 8 carbon atoms, and divalent cycloalkyl group of from about 5 to about 10 carbon atoms, and, more preferably from about 5 to about 8 carbon atoms. More preferably, each R is independently selected from the group consisting of methyl, ethyl or propyl. R* preferably is a linear or branched divalent alkylene group containing from 3 to about 8 carbon atoms such as, for example, propylene, 2-methylpropylene, neopentylene or 2-butyl-2-ethylpropylene.

Some examples of hydroxymethylphosphonates can include dimethyl hydroxymethylphosphonate, diethyl hydroxymethylphosphonate, dipropyl hydroxymethylphosphonate, diisopropyl hydroxymethylphosphonate, methyl ethyl hydroxymethylphosphonate, methyl propyl hydroxymethylphosphonate, methyl isopropyl hydroxymethylphosphonate, ethyl propyl hydroxymethylphosphonate, ethyl isopropyl hydroxymethylphosphonate, propyl isopropyl hydroxymethylphosphonate, dibutyl hydroxymethylphosphonate, dioctyl hydroxymethylphosphonate, propyl pentyl hydroxymethylphosphonate, dicyclohexyl hydroxymethylphosphonate, 1,3,2-dioxaphosphorinane, 5-methyl-2-(hydroxymethyl), 2-oxide; 1,3,2-dioxaphosphorinane, 5,5-dimethyl-2-(hydroxymethyl), 2-oxide; 1,3,2-dioxaphosphorinane, 5-ethyl-6-propyl-2-(hydroxymethyl), 2-oxide; 1,3,2-dioxaphosphorinane, 5,5-dimethyl-6-isopropyl-2-(hydroxymethyl), 2-oxide; 1,3,2-dioxaphosphorinane, 5-butyl-5-ethyl-2-(hydroxymethyl), 2-oxide and combinations thereof.

The dialkyl phosphite herein can be any commercially available dialkyl phosphite and specifically is a dialkyl phosphite of the general formula:

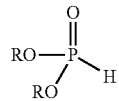

or the general formula:

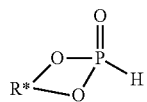

wherein each R is independently the same or different, linear or branched alkyl group of from 1 to about 8 carbon atoms, preferably from 1 to about 6 carbon atoms, and more preferably from 1 to about 3 carbon atoms, linear or branched alkenyl group of from 2 to about 10 carbon atoms, and more preferably from about 3 to about 8 carbon atoms, cycloalkenyl group of from about 5 to about 10 carbon atoms, and more preferably from about 5 to about 8 carbon atoms, and, cycloalkyl group of from about 5 to about 10 carbon atoms, and, more preferably from about 5 to about 8 carbon atoms and R* is a linear or branched divalent alkylene group of from 2 to about 10 carbon atoms, preferably from 3 to about 8 carbon atoms, linear or branched divalent alkenylene group of from 2 to about 10 carbon atoms, and more preferably from about 3 to about 8 carbon atoms, divalent cycloalkenyl group of from about 5 to about 10 carbon atoms, and more preferably from about 5 to about 8 carbon atoms, and divalent cycloalkyl group of from about 5 to about 10 carbon atoms, and, more preferably from about 5 to about 8 carbon atoms. More preferably, each R is independently selected from the group consisting of methyl, ethyl or propyl. R* preferably is a linear or branched divalent alkylene group containing from 3 to about 8 carbon atoms such as, for example, propylene, 2-methylpropylene, neopentylene or 2-butyl-2-ethylpropylene. Some examples of dialkyl phosphite used in the present invention can be obtained from Rhodia and/or United Phosphorus.

Some examples of dialkyl phosphite are selected from the group consisting of dimethyl phosphite, diethyl phosphite, dipropyl phosphite, di-isopropyl phosphite, methyl ethyl phosphite, methyl propyl phosphite, methyl isopropyl phosphite, ethyl propyl phosphite, ethyl isopropyl phosphite, propyl isopropyl phosphite, dibutyl phosphite, diisobutyl phosphite, dioctyl phosphite, propyl pentyl phosphite, dicyclohexyl phosphite and combinations thereof.

The trialkyl phosphite herein can be any commercially available trialkyl phosphite and specifically is a trialkyl phosphite is of the general formula:

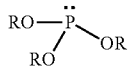

or of the general formula:

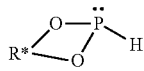

wherein each R is independently the same or different, linear or branched alkyl group of from 1 to about 8 carbon atoms, preferably from 1 to about 6 carbon atoms, and more preferably from 1 to about 3 carbon atoms, linear or branched alkenyl group of from 2 to about 10 carbon atoms, and more preferably from about 3 to about 8 carbon atoms, cycloalkenyl group of from about 5 to about 10 carbon atoms, and more preferably from about 5 to about 8 carbon atoms, and, cycloalkyl group of from about 5 to about 10 carbon atoms, and, more preferably from about 5 to about 8 carbon atoms and R* is a linear or branched divalent alkylene group of from 2 to about 10 carbon atoms, preferably from 3 to about 8 carbon atoms, linear or branched divalent alkenylene group of from 2 to about 10 carbon atoms, and more preferably from about 3 to about 8 carbon atoms, divalent cycloalkenyl group of from about 5 to about 10 carbon atoms, and more preferably from about 5 to about 8 carbon atoms, and divalent cycloalkyl group of from about 5 to about 10 carbon atoms, and, more preferably from about 5 to about 8 carbon atoms. More preferably, each R is independently selected from the group consisting of methyl, ethyl or propyl. R* preferably is a linear or branched divalent alkylene group containing from 3 to about 8 carbon atoms such as, for example, propylene, 2-methylpropylene, neopentylene or 2-butyl-2-ethylpropylene.

Some examples of trialkyl phosphite are selected from the group consisting of trimethyl phosphite, triethyl phosphite, tripropyl phosphite, triisopropyl phosphite, tributyl phosphite, triisobutyl phosphite, tricyclohexyl phosphite, trioctyl phosphite, diethyl methyl phosphite, dimethyl ethyl phosphite, dipropyl methyl phosphite, dimethyl propyl phosphite, dipropyl ethyl phosphite, diethyl propyl phosphite, diisopropyl methyl phosphite, dimethyl isopropyl phosphite, diisopropyl ethyl phosphite, diethyl isopropyl phosphite, dibutyl methyl phosphite, dimethyl butyl phosphite, dibutyl ethyl phosphite, diethyl butyl phosphite, dibutyl propyl phosphite, dipropyl butyl phosphite, dibutyl isobutyl phosphite, diisobutyl butyl phosphite. Some examples of trialkyl phosphite used in the present invention can be obtained from Rhodia and/or United Phosphorus.

The paraformaldehyde is heated to the reaction temperature prior to the addition of alkyl phosphite. Preferably the reaction temperature is from about 25 degrees Celsius to about 75 degrees Celsius, more preferably from about 30 to about 75 degrees Celsius, even more preferably from about 35 to about 60 degrees Celsius, even more preferably from about 35 to about 55 degrees Celsius, yet even more preferably from about 40 degrees to about 55 degrees Celsius, and most preferably from about 45 degrees to about 55 degrees Celsius. Other preferable reaction temperature ranges can be from 35 degrees Celsius to about 65 degrees Celsius or from 30 degrees to about 55 degrees Celsius. In one embodiment the reaction temperature can be from about 45 degrees Celsius to about 52 degrees Celsius. Additionally, the reaction temperature herein can be less than room temperature, for example, from about zero degrees Celsius to about 75 degrees Celsius and any from zero degrees Celsius to any of the reaction temperature endpoints provided herein, such as from about zero degrees Celsius to about 55 degrees Celsius and combinations of any of the endpoints listed herein.

In another embodiment herein, the reaction can be (optionally with a unhindered amine catalyst) run at an elevated temperature of 75 degrees Celsius or greater, preferably from about 75 degrees Celsius to about 200 degrees Celsius, more preferably from about 75 degrees Celsius to about 180 degrees Celsius, and most preferably from about 75 degrees Celsius to about 170 degrees Celsius. In one specific embodiment, the reaction can be run at an elevated temperature of from about 75 to about 150 degrees Celsius.

In a more specific case, the hindered amine catalyst used in the present invention is a tertiary amine in which the nitrogen in the amine is directly bound to a secondary and/or tertiary carbon of an organic group, e.g., an alkyl group of from 1 to about 8 carbon atoms, such a hindered amine catalyst will contain at least one such group, preferably two, and even three. It will be understood herein that the use of the expression secondary and/or tertiary carbon of an organic group indicates that at least one organic group which is bound to the nitrogen is a secondary or tertiary organic group, e.g., a secondary or tertiary alkyl group, wherein the central carbon in said secondary or tertiary alkyl group is directly bound to the nitrogen of the amine. It will be understood that such an organic group may in one embodiment contain more than one secondary or tertiary carbon, provided that one of said secondary or tertiary carbons is directly bound to the nitrogen of the amine.

Preferably, the hindered amine catalyst is of the general formula:

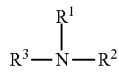

wherein each $R^1$, $R^2$ and $R^3$ is each independently the same or different linear, alkyl group containing from one to about 8 carbon atoms, branched alkyl group containing from 3 to about 8 carbon atoms, linear or branched alkenyl group containing up to about 8 carbon atoms, cyclic alkyl group containing from 5 to about 8 carbon atoms, or an aryl group containing from 6 to about 10 carbon atoms, provided that at least one of the $R^1$, $R^2$ and $R^3$ groups is directly bonded to the amine nitrogen by a secondary and/or tertiary carbon atom of said $R^1$, and/or $R^2$, and/or $R^3$ group. Preferably in the hindered amine catalyst of the above general formula at least two of the $R^1$, $R^2$ and $R^3$ groups are attached via a secondary and/or tertiary carbon, and more preferably all three of the $R^1$, $R^2$ and $R^3$ groups are attached via a secondary and/or tertiary carbon. In one non-limiting embodiment herein, each $R^1$, $R^2$ and $R^3$ group of the above general formula of the hindered amine catalyst is independently the same or different and is selected from the group consisting of methyl, ethyl, propyl, butyl, isopropyl, isobutyl, sec-butyl, tert-butyl, isopentyl, neopentyl, isohexyl, isoheptyl, cyclohexyl and phenyl, provided that at least one of the $R^1$, $R^2$ and $R^3$ groups are selected from the group consisting of isopropyl, sec-butyl, tert-butyl, and cyclohexyl. Preferably, at least two of the $R^1$, $R^2$ and $R^3$ groups are selected from the group consisting of isopropyl, sec-butyl, tert-butyl, and cyclohexyl and most preferably, all three of the $R^1$, $R^2$ and $R^3$ groups are selected from the group consisting of isopropyl, sec-butyl, tert-butyl, and cyclohexyl.

Some non-limiting examples of hindered amine catalyst that can be used herein are those selected from the group consisting of triisopropylamine, tri(sec-butyl)amine, tricyclohexylamine, diisopropylmethylamine, diisopropylethylamine, diisopropylpropylamine, di(sec-butyl)methylamine, di(sec-butyl)ethylamine, di(sec-butyl)propylamine, dicyclohexylmethylamine, dicyclohexylethylamine, dicyclohexylpropylamine, diisopropylisobutylamine, diisopropyl(sec-butyl)amine, diisopropylcyclohexylamine, diisopropylphenylamine, diisobutylisopropylamine, diisobutyl(sec-butyl)amine, diisobutylcyclohexylamine, di(sec-butyl)isopropylamine, di(sec-butyl)isobutylamine, di(sec-butyl)cyclohexylamine, di(sec-butyl)phenylamine, dicyclohexylisopropylamine, dicyclohexylisobutylamine, dicyclohexyl(sec-butyl)amine, dicyclohexylphenylamine, diphenylisopropylamine, diphenyl(sec-butyl)amine, diphenylcyclohexylamine, and combinations thereof.

In another embodiment herein the catalyst used in the method herein can be an unhindered amine catalyst wherein each $R^1$, $R^2$ and $R^3$ is each independently the same or different linear, alkyl group containing from one to about 8 carbon atoms, branched alkyl group containing from 3 to about 8 carbon atoms, linear or branched alkenyl group containing up to about 8 carbon atoms, cyclic alkyl group containing from 5 to about 8 carbon atoms, or an aryl group containing from 6 to about 10 carbon atoms.

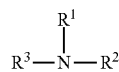

Some non-limiting examples of unhindered amine catalyst that can be used herein are triethylamine, diethylmethylamine, dimethylethylamine, tripropylamine, tributylamine, triisobutylamine and combinations thereof.

The method of the making hydroxymethylphosphonate herein can comprise heating the paraformaldehyde to the reaction temperature followed by adding the dialkyl phosphite and trialkyl phosphite thereto, as described herein with respect to the rate of addition, with solvent and hindered amine catalyst present in the reaction medium and/or mixture.

The amine catalyst finds its employment in the reaction mixture in any manner that is most expedient; provided the herein described rate of addition of dialkyl phosphite and trialkyl phosphite to the paraformaldehyde is maintained (e.g., there is no extreme/significant exotherm), preferably, the amine catalyst is combined with the paraformaldehyde before, during, or after heating the paraformaldehyde, most preferably before said heating. In another less preferable embodiment, the amine catalyst is combined with the dialkyl phosphite and/or trialkyl phosphite before or during the addition to paraformaldehyde. In a preferable embodiment, the amine catalyst is present in a reaction vessel prior to the addition of paraformaldehyde thereto. Still further, in another embodiment, the amine catalyst can be combined in part with the dialkyl phosphite and/or trialkyl phosphite and paraformaldehyde prior to reaction thereof. Similarly, the solvent, if present, can be added to the reaction medium in like manner as described for the amine catalyst, alone or in combination with the amine catalyst. Preferably, the solvent, if present, is added to the paraformaldehyde or the paraformaldehyde is added to the solvent, prior to or during heating of the paraformaldehyde.

Preferably the solvent, if present, can be any solvent which effectively solvates or suspends (with stirring) the paraformaldehyde component. Effective salvation or suspension can vary greatly depending on the solvent and the amount of paraformaldehyde employed in the method herein. Preferably, effective solvation/suspension can comprise sufficient solvent to effect solvation/suspension of from 50 weight percent of the paraformaldehyde, based on the total weight of paraformaldehyde, to an amount of solvent that is up to about 100 percent more solvent than is necessary for the complete dissolution/suspension of the total paraformaldehyde being employed, said latter percent being based upon the total amount of solvent necessary to completely solvate/suspend the total amount of paraformaldehyde being employed. Preferably, the amount of solvent present will be sufficient to solvate/suspend from about 75 weight percent of the paraformaldehyde, up to about 25 percent more solvent than is necessary to completely solvate/suspend the total paraformaldehyde being employed. In one embodiment, solvent is used in at least the amount necessary to completely solvate and/or suspend the amount of paraformaldehyde being used at the reaction temperature being employed.

In one preferable embodiment, the solvent is a hydroxyalkylphosphonate, more preferably a hydroxymethylphosphonate, even more preferably any of the hydroxymethylphosphonates described herein, and most preferably a portion of hydroxymethylphosphonate remaining from a previous batch formed from the reaction method described herein, i.e., a heel of product hydroxymethylphosphonate. In one embodiment, the hydroxyalkylphosphonate can be other than that of a heel of a previous batch. Specifically, the portion of remaining hydroxymethylphosphonate from a previous batch which can effectively operate as a solvent for the paraformaldehyde can comprise from about 0.01 weight percent to about 35 weight percent, preferably from about 5 weight percent to about 30 weight percent, more preferably from about 10 weight percent to about 28 weight percent, and most preferably from about 15 weight percent to about 25 weight percent, said weight percent being based on the total weight of the product hydroxymethylphosphonate of a previous reaction batch that remains in situ, or is provided from the previous reaction vessel.

In another embodiment herein, the solvent can be any other solvent other than hydroxyalkylphosphonate that can effectively solvate/suspend the paraformaldehyde as described above, such as for example, dry solvents. Some non-limiting examples of solvents can comprise toluene, xylene, cyclohexane, n-heptane, hexane, methyl acetate, ethyl acetate, methanol, ethanol, propanol, isopropanol, butanol and combinations thereof.

In one embodiment, the method herein is conducted in the absence of solvent, such as the non-limiting example of wherein any one or more of the amine, the dialkyl phosphite and/or the trialkyl phosphite can function as a medium to allow the reaction of the method herein to occur in the liquid state.

In one other embodiment of the method herein, the dialkyl phosphite and trialkyl phosphite is added to the heated paraformaldehyde at any intermittent and/or continuous rate that will produce the reaction product in a purity greater than 90 percent by weight, more preferably greater than about 95 percent by weight, and most preferably greater than about 99 percent by weight, said weight percent being based on the total weight of product hydroxymethylphosphonate. In one embodiment herein the reaction product hydroxyalkylphosphonate is produced in a purity of greater than 90 percent by weight, preferably greater than 95 percent by weight and most preferably greater than about 99 percent by weight, said percent being based on the total weight of reaction product. Such purity is to the exclusion of side-products, specifically, P-III-based side-products, such as phosphites and alkyl acid phosphites. More specifically exclusion of side products is understood to be less than about 10 percent by weight, more preferably less than about 5 percent by weight and most preferably less than about 1 percent by weight of said side-products, said percent by weight being based on the total weight of the hydroxymethylphosphonate reaction product. It is understood that in one embodiment herein that in addition to the avoidance or inhibition of a significant amount of acid by-product (by preventing or limiting the formation of water), that the rate, order of addition and catalyst choice will avoid and/or inhibit the production of the above recited amounts of side-products. Amounts of side-product in excess of 10 percent by weight will negatively affect the quality of, and/or the ability to make, polyurethane foam made from polyurethane foam-forming compositions containing such side-products.

Preferably, in the method described herein, the method will produce a hydroxymethylphosphonate reaction product wherein the product contains less than about 10 percent by weight of quaternized amine salt and/or free acid derivative of the product, more preferably less than about 5 percent by weight of quaternized amine salt and/or free acid derivative of the product, and most preferably less than about 1 percent by weight of quaternized amine salt and/or free acid derivative of the product based on the total weight of the reaction product.

In one embodiment, the dialkyl phosphite and trialkyl phosphite is added to the heated paraformaldehyde at a rate that maintains the reaction temperature at from about 30 degrees Celsius to about 75 degrees Celsius, more preferably any of the reaction temperature ranges described herein, e.g. above 75 degrees Celsius and below 200 degrees Celsius. Preferably, the dialkyl phosphite and trialkyl phosphite is added to the heated paraformaldehyde at a rate that maintains the reaction temperature at from about 30 degrees Celsius to about 55 degrees Celsius. Alternate range can comprise from about 30 to about 65 degrees Celsius, from about 35 to about 60 degrees Celsius, from about 40 to about 55 degrees Celsius and combinations of any endpoints of said temperature ranges, e.g., from about 30 to about 55 degrees Celsius, and the like.

In one embodiment herein the dialkyl phosphite and trialkyl phosphite is added to the heated paraformaldehyde over a period of from about 10 minutes to about 24 hours, more preferably from about 15 minutes to about 20 hours, even more preferably from about 20 minutes to about 15 hours, yet even more preferably from about 20 minutes to about 10 hours, yet still even more preferably from about 30 minutes to about 8 hours and most preferably from about 45 minutes to about 5 hours. Such time period ranges include all ranges therebetween and any combination of said endpoints. In one embodiment, the dialkyl phosphite and trialkyl phosphite is added to the heated paraformaldehyde over a period of from about 10 minutes to about 5 hours.

While the step of using an elevated temperature is not necessary in the method herein, it can be utilized to force the reaction to completion, i.e., the complete or substantial reaction of any (if any) remaining unreacted components following the completion of the addition. It is understood herein that the optional elevated temperature step, if employed, will employ a temperature that is in excess of the desired reaction temperature. Preferably, the elevated temperature can be from any temperature higher than the chosen reaction temperature up to about 85 degrees Celsius. More preferably the elevated temperature is from about 55 to about 75 degrees Celsius, even more preferably from about 60 to about 75 degrees Celsius, and most preferably from about 65 to about 75 degrees Celsius. The elevated reaction temperature can be maintained from about 1 minute to about 5 hours, preferably from about 5 minutes to about 4 hours, more preferably from about 10 minutes to about 3 hours and most preferably from about 30 minutes to about 2.5 hours.

While the amount of paraformaldehyde and phosphite (phosphite=total amount of dialkyl phosphite and trialkyl phosphite) can vary dramatically depending on the specific reaction components and conditions, solvent (if present), catalyst, desired reaction temperature, and batch size, preferably, the amount of paraformaldehyde and the amount of phosphite can exist in equivalent or near equivalent molar amounts. Near equivalent molar amounts can comprise wherein either the paraformaldehyde or the amount of phosphite is present in a molar excess of the other component(s). Preferably, either the amount of phosphite or the paraformaldehyde component can exist in no more than 15 molar percent excess of the other, more preferably no more than 10 molar percent excess of the other, and most preferably no more than 5 molar percent excess of the other. In one preferable embodiment, the paraformaldehyde can be present in about 1 to about 5 molar percent excess of the molar amount of phosphite.

The amount of trialkyl phosphite can be present in an amount of from about 1 molar percent to about 20 molar percent of the total amount of dialkyl phosphite used in the reaction mixture, preferably from about 5 molar percent to about 15 molar percent of the total amount of dialkyl phosphite used in the reaction mixture, and most preferably from about 8 to about 12 molar percent of the total amount of dialkyl phosphite used in the reaction mixture.

In one non-limiting embodiment, the molar percent of the components of the reaction mixture of dialkyl phosphite, paraformaldehyde, trialkyl phosphite and amine used in the process herein are, dialkyl phosphite in an amount of about 34 to about 52 molar percent, preferably about 39 to about 48 molar percent and most preferably from about 41 to about 46 molar percent; paraformaldehyde in an amount of from about 40 to about 60 molar percent, preferably from about 45 to about 55 molar percent and most preferably from about 48 to about 53 molar percent; trialkyl phosphite in an amount of from about 1 to about 10 molar percent, preferably from about 2 to about 8 molar percent, even more preferably from about 3 to about 6 molar percent and most preferably from about 4 to about 5 molar percent; amine, if present, in an amount of from about 0.1 to about 5 molar percent, preferably from about 0.1 to about 3.0 molar percent, even more preferably from about 0.5 to about 2.0 molar percent and most preferably from about 0.8 to about 1.2 molar percent, said molar percent of each of the noted components of the reaction mixture used in the process herein being based on the total molar amount of all of the components of the reaction mixture used in the process herein.

The solvent, if present, can be present in the solvating ranges described above but preferably about 5 to about 40 weight percent, more preferably from about 10 to about 30 weight percent and most preferably, from about 15 to about 25 weight percent, said weight percent being based on the total weight of the reaction mixture. The catalyst can be used in amounts of preferably from about 0.1 to about 3.0 molar percent, more preferably from about 0.5 to about 2.0 molar percent, and most preferably from about 0.8 to about 1.2 molar percent in relation to the other reaction ingredients.

Advantageously, the reaction herein can be conducted in a large batch. Preferably, the large batch comprises wherein the amount of reaction product produced comprises from 0.22 pounds up to about 75,000 pounds, more preferably from about 2.2 pounds up to about 65,000 pounds, even more preferably from about 220 pounds up to about 55,000 pounds and most preferably from about 2,200 pounds up to about 50,000 pounds.

The hydroxymethylphosphonate reaction product herein can be advantageously utilized in polyurethane foam-forming compositions as a flame-retardant for the polyurethane foam formed therefrom and/or as a polyol component in the polyurethane-foam forming composition. Such polyurethane foam-forming compositions, and those described herein, made using the hydroxymethylphosphonate made by the method described herein, can be reacted to form polyurethane foams, which foams can be utilized in the construction and formation of various articles such as furniture, bedding, automotive seat cushions, panel, and pour-in-place and spray foam insulation.

In one embodiment, the product hydroxymethylphosphonate contains an amount of water of less than about 1.0 wt %, preferably, less than about 0.5 wt % and most preferably less than about 0.1 wt % of water based on the total weight of the reaction product mixture. In one embodiment, the amount of water in the product hydroxymethylphosphonate is less than the amount of water in a hydroxymethylphosphonate made by an equivalent process which did not contain at least one trialkyl phosphite.

In another embodiment, the product hydroxymethylphosphonate can have a longer shelf life than a hydroxymethylphosphonate made by an equivalent process which did not contain at least one trialkyl phosphite. Shelf life expiration is defined as reaching a maximum acidity of the product in milligrams KOH per gram of product (mg KOH/g) after a specified length of time of storage at 25 degrees Celsius. In one embodiment, the shelf life of the hydroxymethylphosphonate product is such that it will have an acidity less than 15 mg KOH per gram after 12 months of storage at 25 degrees Celsius, preferably less than 10 mg KOH per gram after 12 months of storage at 25 degrees Celsius and most preferably less than 8 mg KOH per gram after 12 months of storage at 25 degrees Celsius.

These stable low acidity and low water-containing products are advantageous in that the use of a high acid reaction product in foam neutralizes the amine catalysts normally used in making the foam preventing the normal foam-making process. The production of low water containing products ensures product storage stability, while at the same time eliminates the concern that water in the product will act as a blowing agent in the foaming process. In many cases, foam cannot be made with these high acidity and high water containing products. Heretofore hydroxymethylphosphonates made by prior art methods were either not used in polyurethane foam-forming compositions due to the poor quality of foams made by such prior art methods or such hydroxymethylphosphonates required the extensive additional step of purifying the phosphonate ester of any acidity, water contamination and/or side-products prior to their use in polyurethane foam forming compositions and the articles made therefrom, where said purification step(s) dramatically increase the complexity of making polyurethane foams and/or additionally increase the costs of making such foams.

The present invention avoids these previously required steps and provides a hydroxymethylphosphonate ester that can be directly used in polyurethane-foam forming compositions and applications without further purification steps, e.g., distillation.

In one embodiment herein the method herein can result in a product hydroxymethylphosphonate with a lower acid number and lower water content than a hydroxymethylphosphonate made by an equivalent process which did not contain at least one trialkyl phosphite. Specifically, the hydroxymethylphosphonate made by the method described herein has an acidity of less than about 8 mg KOH/g, more preferably, less than about 6 mg KOH/g, and most preferably, less than about 4 mg KOH/g; additionally a water content less than about 1.0 wt %, more preferably, less than about 0.5 wt %, and most preferably, less than about 0.1 wt %.

In one embodiment herein, the product hydroxymethylphosphonate can be used in a polyurethane foam-forming composition without further purification. Preferably, the product hydroxymethylphosphonate can be used in a polyurethane foam-forming composition without further purification when the solvent (if present) comprises a heel of hydroxymethylphosphonate from a previous batch as described herein. The heel of hydroxymethylphosphonate avoids and/or reduces any purification that can be necessary or desirable prior to use of the hydroxymethylphosphonate reaction product in polyurethane foam-forming compositions. If a solvent (if used) other than hydroxyalkylphosphonate is used herein then, preferably, distillation or any other known purification method can be used prior to use in a polyurethane foam-forming composition to remove the solvent.

Advantageously, the amine catalyst of the method herein (hindered or unhindered) can be utilized as the catalyst in a polyurethane foam-forming composition, which comprises, polyol (or a hydroxyl-containing component), isocyanate and catalyst. Preferably, the hydroxymethylphosphonate reaction product of the method described herein and the amine catalyst of the method herein can remain in situ and be used in the polyurethane foam-forming composition or can be transferred to another reaction vessel where they are used in a polyurethane reaction-forming composition.

Preferably there is provided herein a polyurethane foam-forming composition comprising a polyol, an isocyanate, a catalyst and the hydroxymethylphosphonate produced by the method described herein. Alternatively, there is also preferably provided a polyurethane foam-forming composition comprising a polyol, an isocyanate, and both the amine catalyst and the product hydroxymethylphosphonate of the method described herein. Further there is provided a polyurethane foam-forming composition comprising an isocyanate, a catalyst and the hydroxymethylphosphonate made by the method herein, wherein the hydroxymethylphosphonate functions as an additional hydroxyl-containing component and/or a flame retardant in the polyurethane foam-forming composition.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above.

EXAMPLES

Example #1

Diethyl Hydroxymethylphosphonate Synthesis

Reaction Procedure Incorporating Triethyl Phosphite as an Acid/Water Reducer and Using Triethylamine as the Amine Catalyst (Extreme Exotherm)

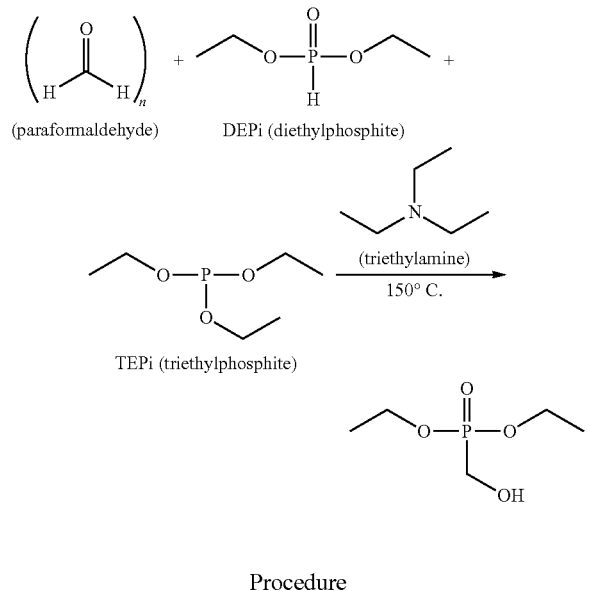

Procedure

Diethyl phosphite (186.4 grams, 173.9 ml, 1.35 moles, Acid #=2.0 mg KOH/g), triethyl phosphite (24.9 grams, 25.7 ml, 0.15 moles), 49.7 grams of 95% reagent grade paraformaldehyde powder (1.58 moles of paraformaldehyde) and 5.6 grams of triethylamine (7.7 ml, 0.055 moles) were added to a 1000 ml round bottom flask equipped with reflux condenser, magnetic stirrer, heating mantle, temperature monitor and $N_2$ inlet. The reaction was stirred to give a milky mixture. The reaction mixture was heated to 30-40° C., where the reaction mixture began to exotherm. The temperature of the reaction mixture reached a maximum of 150° C. within ~30 seconds to yield a colorless solution. Once the exotherm subsided, the reaction mixture was cooled with stirring to room temperature. A sample was taken out for water content and acid number analysis. The results are shown below.

Analytical Results
Acid #=3.5 mg KOH/g
Water=650 ppm

Comparative Example #1

Diethyl Hydroxymethylphosphonate Synthesis

Reaction Procedure Using Triethylamine as the Amine Catalyst (Extreme Exotherm)

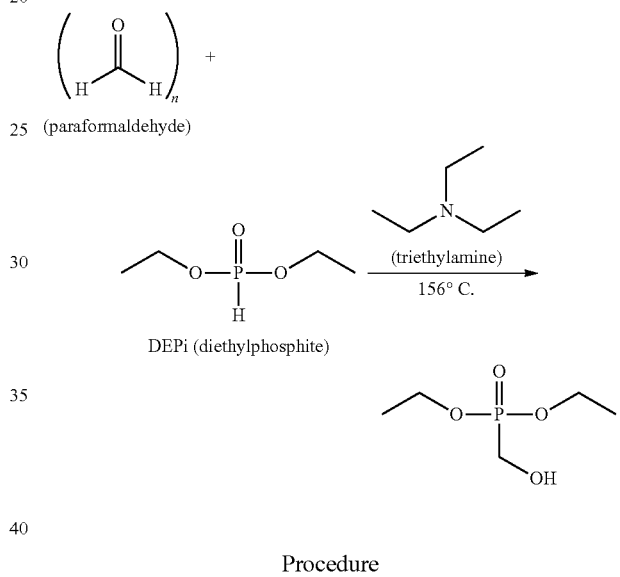

Procedure

Diethyl phosphite (207.1 grams, 193.2 ml, 1.50 moles, Acid #=2.0 mg KOH/g), 49.7 grams of 95% reagent grade paraformaldehyde powder (1.58 moles of paraformaldehyde) and 5.6 grams of triethylamine (7.7 ml, 0.055 moles) were added to a 1000 ml round bottom flask equipped with reflux condenser, magnetic stirrer, heating mantle, temperature monitor and $N_2$ inlet. The reaction was stirred to give a milky mixture. The reaction mixture was heated to 30-40° C., where the reaction mixture began to exotherm. The temperature of the reaction mixture reached a maximum of 156° C. within ~30 seconds to yield a colorless solution. Once the exotherm subsided, the reaction mixture was cooled with stirring to room temperature. A sample was taken out for water content and acid number analysis. The results are shown below.

Analytical Results
Acid #=10.0 mg KOH/g
Water=5320 ppm

Example #2

Diethyl Hydroxymethylphosphonate Synthesis

Reaction Procedure Incorporating Triethyl Phosphite as an Acid/Water Reducer and Using Diisopropylethylamine as a Hindered Amine Catalyst (Controlled Addition/Exotherm)

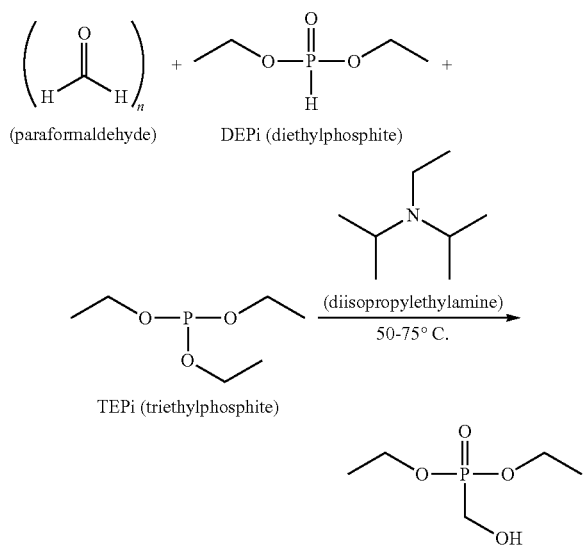

(paraformaldehyde)   DEPi (diethylphosphite)

TEPi (triethylphosphite)

Procedure

The reaction heal (50 ml of diethyl hydroxymethylphosphonate, Acid #=7.8 mg KOH/g) was added to a 1000 ml reactor vessel equipped with a reflux condenser, magnetic stirrer, heating mantle, temperature monitor and $N_2$ inlet, followed by the addition of 49.7 grams of 95% reagent grade paraformaldehyde powder (1.58 moles of paraformaldehyde). After heating the reaction mixture to 50° C., 4.5 grams of diisopropylethylamine (6.1 ml, 0.035 moles) were added to the reactor, followed by the slow addition of a mixture of 186.4 grams of diethyl phosphite (173.9 ml, 1.35 moles, Acid #=2.0 mg KOH/g) and 24.9 grams of triethyl phosphite (25.7 ml, 0.15 moles). The phosphite addition was completed in 1.5 hours at a rate of 2.3 grams/minute. The reaction temperature was maintained at 50° C. throughout the addition. After completing the addition, the reaction temperature was raised to 75° C. and held for 1-2 hours or until all of the diethyl phosphite was consumed as indicated by $P^{31}$ NMR. Once the reaction was complete, the reaction mixture was cooled with stirring to room temperature. A sample was taken out for water content and acid number analysis. The results are shown below.

Analytical Results
Acid #=2.6 mg KOH/g
Water=1140 ppm

Comparative Example #2

Diethyl Hydroxymethylphosphonate Synthesis

Reaction Procedure Using Diisopropylethylamine as a Hindered Amine Catalyst (Controlled Addition/Exotherm)

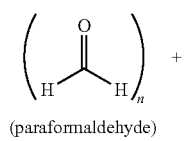

(paraformaldehyde)

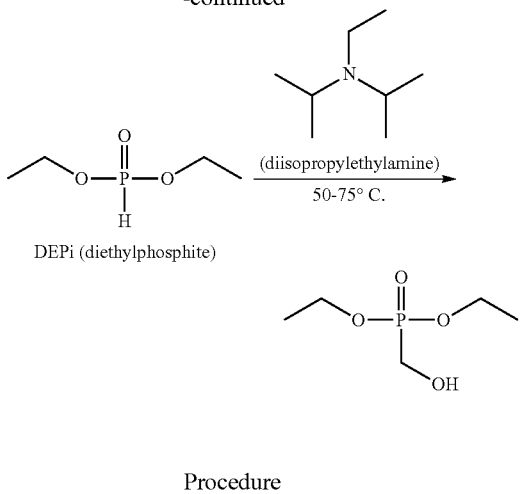

DEPi (diethylphosphite)

Procedure

The reaction heal (50 ml of diethyl hydroxymethylphosphonate, Acid #=7.8 mg KOH/g) was added to a 1000 ml reactor vessel equipped with a reflux condenser, magnetic stirrer, heating mantle, temperature monitor and $N_2$ inlet, followed by the addition of 49.7 grams of 95% reagent grade paraformaldehyde powder (1.58 moles of paraformaldehyde). After heating the reaction mixture to 50° C., 4.5 grams of diisopropylethylamine (6.1 ml, 0.035 moles) were added to the reactor, followed by the slow addition of 207.1 grams of diethyl phosphite (193.2 ml, 1.50 moles, Acid #=2.0 mg KOH/g). The diethyl phosphite addition was completed in 1.5 hours at a rate of 2.3 grams/minute. The reaction temperature was maintained at 50° C. throughout the addition. After completing the addition, the reaction temperature was raised to 75° C. and held for 1-2 hours or until all of the diethyl phosphite was consumed as indicated by $P^{31}$ NMR. Once the reaction was complete, the reaction mixture was cooled with stirring to room temperature. A sample was taken out for water content and acid number analysis. The results are shown below.

Analytical Results
Acid #=6.7 mg KOH/g
Water=13000 ppm

| PRODUCT SAMPLE | ACID NUMBER (mg KOH/g) | WATER CONTENT (ppm) |
|---|---|---|
| Example #1 | 3.5 | 650 |
| Comparative Example #1 | 10.0 | 5320 |
| Example #2 | 2.6 | 1140 |
| Comparative Example #2 | 6.7 | 13000 |

The invention claimed is:

1. A method of making hydroxymethylphosphonate comprising reacting paraformaldehyde, at least one dialkyl phosphite of the general formula:

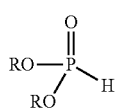

or the general formula:

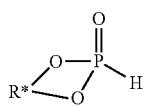

and at least one trialkyl phosphite of the general formula:

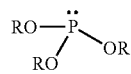

or of the general formula:

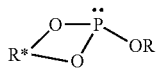

wherein each R is independently the same or different, linear or branched alkyl of from 1 to about 8 carbon atoms, linear or branched alkenyl group of from 2 to about 10 carbon atoms, cycloalkenyl group of from about 5 to about 10 carbon atoms, and, cycloalkyl group of from about 5 to about 10 carbon atoms; and R* is a linear or branched divalent alkylene group of from 2 to about 10 carbon atoms, linear or branched divalent alkenylene group of from 2 to about 10 carbon atoms, divalent cycloalkenyl group of from about 5 to about 10 carbon atoms, and divalent cycloalkyl group of from about 5 to about 10 carbon atoms, in the presence of at least one amine catalyst to produce a hydroxymethylphosphonate with a lower acid content than an equivalent method which is conducted in the absence of trialkylphosphite.

2. The method of claim 1 wherein the step of reacting further comprises:
(a) heating paraformaldehyde in a solvent to a desired reaction temperature, wherein the solvent is present in at least an amount necessary to solvate or suspend the paraformaldehyde;
(b) adding at least one dialkyl phosphite and at least one trialkyl phosphite to the heated paraformaldehyde, to provide hydroxymethylphosphonate, there being present in the reaction medium at least one amine catalyst; and, optionally, following the completion of the addition,
(c) heating the reaction mixture to an elevated temperature.

3. The method of claim 2 wherein the dialkyl phosphite and trialkyl phosphite are added to the heated paraformaldehyde at a rate which will produce the product hydroxymethylphosphonate in a purity of greater than 90 percent by weight.

4. The method of claim 1 wherein the amount of trialkyl phosphite is from about 1 weight percent to about 40 weight percent based on the total weight of the dialkyl phosphite in the reaction mixture.

5. The method of claim 1 wherein the amount of trialkyl phosphite is from about 10 weight percent to about 30 weight percent based on the total weight of the dialkyl phosphite in the reaction mixture.

6. The method of claim 2 wherein the solvent is hydroxyalkylphosphonate.

7. The method of claim 1 wherein the hydroxymethylphosphonate is of the general formula:

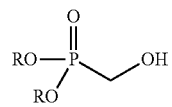

or, the general formula:

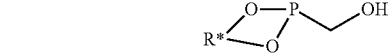

wherein each R is independently the same or different, linear or branched alkyl group of from 1 to about 8 carbon atoms, linear or branched alkenyl group of from 2 to about 10 carbon atoms, cycloalkenyl group of from about 5 to about 10 carbon atoms, and cycloalkyl group of from about 5 to about 10 carbon atoms; and R* is a divalent linear or branched alkylene group of from 2 to about 10 carbon atoms, linear or branched divalent alkenylene group of from 2 to about 10 carbon atoms, divalent cycloalkenyl group of from about 5 to about 10 carbon atoms, and divalent cycloalkyl group of from about 5 to about 10 carbon atoms.

8. The method of claim 2 wherein the amine catalyst is a hindered amine catalyst which is a tertiary amine in which the nitrogen in the amine is directly bound to a secondary and/or tertiary carbon of an organic group.

9. The method of claim 2 wherein the amine catalyst is a hindered amine catalyst of the general formula:

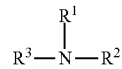

wherein each $R^1$, $R^2$ and $R^3$ is each independently the same or different linear alkyl group containing from one to about 8 carbon atoms, branched alkyl group containing from 3 to about 8 carbon atoms, linear or branched alkenyl group containing up to about 8 carbon atoms, cyclic alkyl group containing from 5 to about 8 carbon atoms, or an aryl group containing from 6 to about 10 carbon atoms, provided that at least one of the $R^1$, $R^2$ and $R^3$ groups are bonded to the nitrogen via a secondary or tertiary carbon of the and/or $R^2$ and/or $R^3$ group.

10. The method of claim 1 wherein the product hydroxymethylphosphonate contains a lower level of water than a hydroxymethylphosphonate made by an equivalent process which did not contain at least one trialkyl phosphite.

11. The method of claim 1 wherein the method is conducted at a temperature at or above 75 degrees Celsius.

12. The method of claim 1 wherein the method is conducted at a temperature of from 30 to about 75 degrees Celsius.

13. The method of claim 1 wherein the method is conducted in the absence of solvent.

14. The method of claim 1 wherein the product hydroxymethylphosphonate has a longer shelf life than a hydroxymethylphosphonate made by an equivalent process which did not contain at least one trialkyl phosphite.

* * * * *